United States Patent
Shibuya et al.

(10) Patent No.: US 6,962,812 B2
(45) Date of Patent: Nov. 8, 2005

(54) CULTURE MEDIUM FOR CULTURE OF ANIMAL CELL AND METHOD FOR PRODUCING PROTEIN USING SAME

(75) Inventors: Kazushi Shibuya, Tokyo (JP); Masaru Atsumi, Tokyo (JP); Shigeyuki Tsunakawa, Tokyo (JP); Kaneo Nogaki, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/336,825

(22) Filed: Jan. 6, 2003

(65) Prior Publication Data

US 2003/0096372 A1 May 22, 2003

Related U.S. Application Data

(62) Division of application No. 09/701,518, filed as application No. PCT/JP99/02904 on Jun. 1, 1999, now Pat. No. 6,537,782.

(30) Foreign Application Priority Data

Jun. 1, 1998 (JP) .......................................... 10-150957

(51) Int. Cl.$^7$ .......................... C12N 5/00; C07K 14/46; C07K 1/12; C12P 21/04; A61K 35/60
(52) U.S. Cl. ...................... 435/325; 424/523; 435/70.1; 530/300; 530/350
(58) Field of Search .......................... 424/523; 530/300, 530/350; 435/70.1, 325

(56) References Cited

U.S. PATENT DOCUMENTS

| 3,856,627 A | | 12/1974 | Nagasawa et al. |
| 3,962,425 A | * | 6/1976 | Oita et al. ................ 424/94.21 |
| 5,426,045 A | | 6/1995 | Sawyer et al. |

FOREIGN PATENT DOCUMENTS

| JP | 49 54581 A | 5/1974 |
| JP | 1 148181 A | 6/1989 |
| JP | 2 39882 A | 2/1990 |
| JP | 6 38704 A | 2/1994 |
| WO | WO 95 23212 | 8/1995 |

OTHER PUBLICATIONS

SigmaChemical Company Catalog Cell Culture Reafgents, 1992, pp. 246–253 and 268–270.

DATABASE WPI, Week 200140, Derwent Publications Ltd., London, GB: AN 2001-375305 40, XP002214165 & CN 1 157 694 A, Aug. 27, 1997 abstract.

Snook, J.T., *Nutrition–A guide to Decision Making*, 1984, p. 449, Prentice Hall, Englewood–Cliffs, N.J.

* cited by examiner

Primary Examiner—Ralph Gitomer
Assistant Examiner—Kailash C. Srivastava
(74) Attorney, Agent, or Firm—Foley & Lardner LLP

(57) ABSTRACT

A culture medium for culture of an animal cell, characterized by containing an enzymatic degradation product of fish meat or a fish meat extract, and a method for producing a desired protein with the use of the culture medium.

8 Claims, 2 Drawing Sheets

CULTURE MEDIUM FOR CULTURE OF ANIMAL CELL AND METHOD FOR PRODUCING PROTEIN USING SAME

This application is a divisional of application Ser. No. 09/701,518, filed Nov. 30, 2000, now U.S. Pat. No. 6,537,782 filed Jun. 1, 1999, which is a national stage application of PCT/JP99/02904.

TECHNICAL FIELD

This invention relates to a culture medium for culture of an animal cell, and a method for producing a protein using it. More specifically, the invention relates to a culture medium for culture of an animal cell, the culture medium containing a fish meat extract or an enzymatic degradation product of fish meat, but not containing a mammal-derived component such as a protein or its decomposition product; and a method for producing a protein using the culture medium.

BACKGROUND ART

In culturing an animal cell to obtain a natural protein produced by the animal cell, or in culturing an animal cell incorporating a gene coding for a desired protein to produce the desired protein, etc., essential nutrients, such as bases, sugars, amino acids, and vitamins, are added to a culture medium. Further, a mammal-derived extract, concretely, serum such as fetal bovine serum, is usually added in a range of 5 to 20% for proliferation of the animal cell. However, such mammal-derived serum has a number of drawbacks. It accounts for 75 to 95% of the cost for the culture medium, and because of inter-lot differences existing in quality, stable proliferation is not achieved. Moreover, the mammal-derived serum cannot be sterilized in an autoclave or the like, and thus may be contaminated with viruses or mycoplasmas. Although most of these viruses or mycoplasmas are nonpathogenic, they can become additional unknown factors from the point of view of stable manufacture. Furthermore, the serum contains more than 500 types of proteins, thus complicating the isolation and purification of the desired protein, the cell product, from the cultured medium. To resolve such problems with stable manufacture, methods using a serum-derived purified protein such as fetuin, insulin or transferrin, instead of serum, are performed. Methods, which use culture medium components extracted from mammals, are also attempted from the viewpoint of production cost.

In recent years, concern has been expressed over the relation of mammal-derived components to mad cow disease, bovine spongiform encephalopathy (BSE), transmissible spongiform encephalopathy (TSE), and Creutzfeld-Jakob disease (CJD). The development of a culture medium for culture of an animal cell, the culture medium being free from these mammal-derived components, has been demanded from the aspect of safety.

In culturing an animal cell, the failure to add the above-described mammal-derived components into the culture medium causes a marked drop in the survival rate of cells, and a decrease in viable cell count in the culture broth, at an early stage of culture. These events make long-term culture or large-scale culture impossible. The present invention aims at providing a culture medium for culture of an animal cell, the culture medium containing no mammal-derived components and freed from the above problems, and a method for producing a protein with the use of the culture medium.

DISCLOSURE OF THE INVENTION

To attain the foregoing object, the inventors of the present invention removed mammal-derived components from conventional culture media for culture of animal cells. They added various substances to the resulting culture media, and conducted an extensive study using a CHO cell transformed with a gene encoding an antibody protein. The purpose of the study was to obtain a substance which would stimulate the proliferation of the CHO cell, thereby producing a high concentration of the antibody protein. The study led to the finding that the purpose could be achieved by adding a fish meat extract or an enzymatic degradation product of fish meat, and based on this finding, the present invention was accomplished.

That is, the invention relates to a culture medium for culture of an animal cell, the culture medium containing a fish meat extract or an enzymatic degradation product of fish meat, and a method for producing a protein with the use of the culture medium.

BEST MODE FOR CARRYING OUT THE INVENTION

Figure 1:
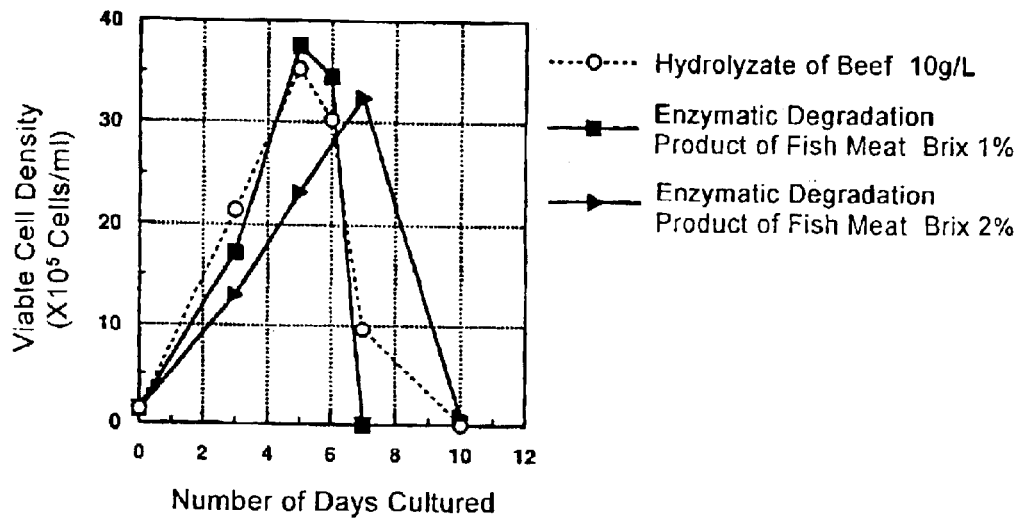
FIG. 1 is a graph showing the viable cell density of CHO cells cultured in culture media containing Brix 1% and Brix 2% of a fish meat enzymatic degradation product, and 10 g/L of a beef hydrolyzate, respectively.
Figure 2:
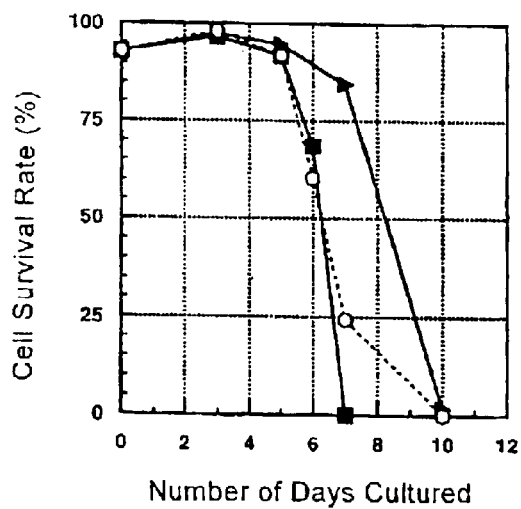
FIG. 2 is a graph showing the survival rates (%) of CHO cells cultured in culture media containing Brix 1% and Brix 2% of a fish meat enzymatic degradation product, and 10 g/L of a beef hydrolyzate, respectively.
Figure 3:
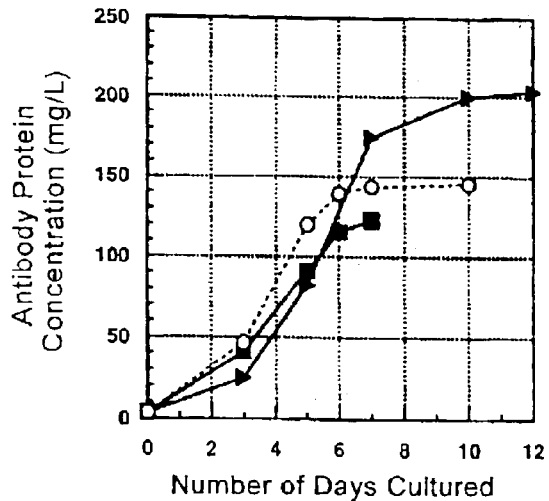
FIG. 3 is a graph showing the concentrations (mg/L) of an antibody protein produced in culture media by CHO cells which were cultured in the culture media containing Brix 1% and Brix 2% of a fish meat enzymatic degradation product, and 10 g/L of a beef hydrolyzate, respectively.

The present invention will be described in detail below. All the documents described herein will be cited herein by reference.

The culture medium of the invention is a culture medium for culture of an animal cell, the culture medium containing a fish meat extract or an enzymatic degradation production of fish meat. According to the invention, an animal cell can be cultured satisfactorily without the addition of mammal-derived components in a culture medium which has generally been used as a culture medium for culture of an animal cell.

Examples of the fish meat used in the invention are the fish meat of red fleshed fishes, such as bonito, frigate mackerel, tuna, mackerel, pacific saury, sardine, horse mackerel, and salmon, and the fish meat of white fleshed fishes, such as cod, Japanese sea bass, right-eyed flounder, left-eyed flounder, and sea bream. The preferred examples are bonito, frigate mackerel, cod, mackerel, salmon, and sardine.

The fish meat extract used in the invention can be obtained by cutting the fish meat into suitable pieces, or mincing the fish meat into a pasty form, and extracting soluble components of the pieces or the paste with hot water, for example, hot water at 90 to 95° C., for several tens of minutes to several tens of hours. Concrete examples are stock made from boiled bonito for production of dried bonito, and cook drain during production of canned foods.

The enzyme degradation product of fish meat can be obtained, for example, by adding a suitable amount of water to cooked fish meat as such, or fish meat minced to a paste, or the above fish meat extract, followed, if necessary, by heating for protein denaturation, then treating the material with a protease, and centrifuging or filtering the treated material as desired, to remove oils and insolubles. The resulting fish meat extract or the enzymatic degradation product of fish meat is desirably adjusted to pH 7 to 7.4 for usage.

The protease used in the invention is, for example, a proteinase and/or a peptidase. In the invention, the term proteinase refers to an enzyme which hydrolyzes a protein as a substrate, while the term peptidase refers to a peptide bond hydrolase for a peptide as a substrate. That is, the activity of the protease against the protein substrate can be distinguished as proteinase activity, while the activity of the protease against the peptide substrate can be distinguished as peptidase activity. When catalyzing cleavage of a peptide bond chain, at its intermediate site, by the activity of protease against the protein substrate, the term proteinase is used. Hence, endopeptidase is used herein as one of proteinases.

Examples of enzymes to be used are enzymes of plant origin, such as papain, chymopapain, bromelain, and ficin, and enzymes from microorganisms, such as molds, bacteria, and yeast. They include endopeptidase, exopeptidase, aminopeptidase, carboxypeptidase, and dipeptidase. These enzymes can be used alone or in combination. When they are combined, they may be added at the same time, or progressively.

The enzymatic degradation product of fish meat in the present invention is preferably an enzymatic degradation product of fish meat obtained by treatment with the proteinase, followed by treatment with the peptidase.

The conditions for treatment with the enzyme differ according to the type of the enzyme used. Usually, the enzyme treatment is performed for 30 minutes to 72 hours, preferably 3 to 24 hours, at pH 2 to 12, preferably pH 4 to 8, at 30 to 90° C., preferably 40 to 65° C. The enzyme is used in a proportion of about 0.01 to 10%, preferably 0.5 to 5%, more preferably 1 to 3%, based on the protein as the substrate.

The enzyme in the resulting enzymatic degradation product of fish meat is inactivated by heating or the like, and performing centrifugation or filtration as desired, to remove oils and insolubles, whereby the enzymatic degradation product can be prepared.

As other components of the culture medium of the invention, various components usually used in animal cell culture media can be used as desired. They include amino acids, vitamins, lipid factors, energy sources, osmotic regulators, iron sources, and pH regulators. In addition to these components, trace metal elements, surfactants, growth cofactors, and nucleosides may be added.

Examples are amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$, and ascorbic acid, preferably, biotin, folic acid, lipoic acid, nicotinamide, calcium pantothenate, pyridoxal hydrochloride, riboflavin, thiamine hydrochloride, vitamin $B_{12}$, and ascorbic acid; lipid factors, such as choline chloride, choline tartrate, linoleic acid, oleic acid, and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium bicarbonate, calcium chloride, sodium phosphate monobasic, HEPES, and MOPS, preferably, sodium bicarbonate. Culture media containing any of these components can be cited as examples.

Besides the above components, there may be added trace metal elements, such as copper sulfate, manganese sulfate, zinc sulfate, magnesium sulfate, nickel chloride, tin chloride, magnesium chloride, and sodium subsilicate, preferably, copper sulfate, zinc sulfate, and magnesium sulfate; surfactants, such as Tween 80, and Pluronic F68; growth cofactors, such as recombinant insulin, recombinant IGF, recombinant EGF, recombinant FGF, recombinant PDGF, recombinant TGF-α, ethanolamine hydrochloride, sodium selenite, retinoic acid, and putrescine dihydrochloride, preferably, sodium selenite, ethanolamine hydrochloride, recombinant IGF, and putrescine dihydrochloride; and nucleosides, such as deoxyadenosine, deoxycytidine, deoxyguanosine, adenosine, cytidine, guanosine, and uridine. In preferred embodiments of the present invention, antibiotics, such as streptomycin, penicillin-G potassium, and gentamicin, and pH-indicators, such as Phenol Red, may be contained.

To prepare the culture medium of the invention concretely, the fish meat extract, or the enzymatic degradation product of fish meat may be added, instead of mammal-derived components, to a commercially available culture medium for culture of an animal cell, for example, BME medium, MEM medium, DMEM medium, F10 medium, or F12 medium.

In the invention, the fish meat extract, or the enzymatic degradation product of fish meat is added to the culture medium to a concentration of approximately Brix 5% or less, preferably Brix 0.5 to 3%, particularly preferably Brix 1 to 2%, in the culture medium. This concentration is a concentration determined by the soluble solids, as an index, measured with a refractometer for sugar content.

The amounts of the other components in the culture medium are 0.05 to 1,500 mg/L for amino acids, 0.001 to 10 mg/L for vitamins, 0 to 200 mg/L for lipid factors, 1 to 20 g/L for energy sources, 0.1 to 10,000 mg/L for osmotic regulators, 0.1 to 500 mg/L for iron sources, 1 to 10,000 mg/L for pH buffers, 0.00001 to 200 mg/L for trace metal elements, 0 to 5,000 mg/L for surfactants, 0.05 to 10,000 µg/L for growth cofactors, and 0.001 to 50 mg/L for nucleosides. Their amounts can be determined, as required, according to the type of the animal cell to be cultured, and the type of the desired protein.

The pH of the culture medium differs according to the cell to be cultured, but is generally pH 6.8 to 7.6, or pH 7.2 to 7.4 in many cases.

The culture medium of the invention can be used, without any restriction, for preferably culturing various animal cells. For example, there can be cultured a COS cell or CHO cell having a gene for the desired antibody or physiologically active substance incorporated by a genetic engineering procedure, or an antibody-producing fused cell typified by a hybridoma, such as mouse-human, mouse-mouse, or mouse-rat. The culture medium is particularly preferred for culture of a CHO cell. Needless to say, the culture medium for culture of an animal cell according to the invention can be used when culturing an animal cell to obtain a natural protein produced by the animal cell. The culture medium can be used for culture of a BHK cell and a HeLa cell as well as the above-mentioned cells.

The culture conditions differ according to the type of the cell used, and preferred conditions may be determined as desired. The CHO cell, for example, is usually cultured for 1 to 14 days in an atmosphere with a $CO_2$ concentration in a gas phase of 0 to 40%, preferably 2 to 10%, at 30 to 39° C., preferably about 37° C.

Culture can be performed using various culture devices for animal cell culture, for example, a fermentor type tank culture device, an air lift type culture device, a culture flask type culture device, a spinner flask type culture device, a microcarrier type culture device, a fluidized bed type culture device, a hollow fiber type culture device, a roller bottle type culture device, and a packed bed type culture device.

By performing culture in the culture medium for culture of an animal cell according to the invention, a protein produced by the animal cell can be obtained in the culture medium. To produce the protein from the animal cell, mere culture may suffice, or a special procedure may be required. The procedure, conditions, etc. may be determined, as required, according to the animal cell to be cultured. In the case of a CHO cell transformed with a vector containing a gene encoding a mouse-human chimeric antibody by a genetic engineering operation, for example, culture is performed under the aforementioned conditions, whereby the desired protein can be obtained in the culture medium in about 1 to 14 days, preferably in about 7 to 10 days. Then, the culture medium is subjected to isolation and purification by customary methods (see, for example, Introduction to Antibody Engineering, Chijin Sho Kan publishing company, pp. 102–104; Affinity Chromatography Principles & Methods, Amersham Pharmacia Bitech, pp. 56–60), whereby the desired protein can be obtained.

The foregoing methods for production can produce gene recombinant proteins, such as recombinant antibodies such as anti-human IL-6 receptor antibody (including chimeric antibodies, humanized antibodies, human antibodies), granulocyte colony stimulating factor (G-CSF), granulocyte macrophage colony stimulating factor (GM-CSF), erythropoietin, interferon, interleukins (e.g., IL-1 and IL-6), t-PA, urokinase, serum albumin, and blood coagulation factor VIII.

INDUSTRIAL APPLICABILITY

The culture medium for culture of an animal cell according to the present invention contains a fish meat extract or an enzymatic degradation product of fish meat, thus making it possible to culture an animal cell stably, without using an expensive protein which varies greatly variation in quality, such as fetal bovine serum. Furthermore, by culturing an animal cell in the culture medium for culture of an animal cell according to the invention, i.e., the culture medium containing a fish meat extract or an enzymatic degradation product of fish meat, the risk of contamination by abnormal prion or viruses, the problem which has arisen in recent years, can be eliminated, and safe biotechnological products can be produced and provided.

EXAMPLES

Examples for describing the present invention in further detail will be shown below, but the invention is in no way limited to these Examples. Various changes and modifications can be made by persons skilled in the art, and they are also included in the scope of the invention.

Example 1

Preparation of Fish Meat (Sardine) Extract

A commercially available sardine was used as fish meat. To 500 g of minced fish meat, 2,500 g of water was added, and the meat was extracted for 90 minutes at a temperature of 95° C.

Then, the extract was centrifuged and filtered to remove insolubles and oils. The residue was concentrated to obtain 64 g of a fish meat (sardine) extract.

Example 2

Preparation of an Enzymatic Degradation Product of Fish Meat (Bonito)

A commercially available bonito was used as fish meat. To 1,000 g of a minced bonito, 1,500 g of water was added. The mixture was incubated for 1 hour together with 4 g of plant-derived papain at pH 6.0 and 50° C. for enzymatic degradation. Then, enzymatic degradation was further carried out with 4 g of mold-derived exopeptidase for 20 hours under the above conditions, whereafter the system was heated at 95° C. to inactivate the enzymes. Then, the system was centrifuged and filtered to remove insolubles and oils. The residue was concentrated to obtain 500 g of an enzymatic degradation product of fish meat (bonito) according to the invention.

Example 3

Preparation of Culture Medium

Thymidine and hypoxanthine were removed from a commercially available DMEM/F12 medium (GIBCO BRL Products and Reference Guide, pp. 357–358). To the resulting medium, the following components were added (the mixture will be described hereinafter as Culture Medium A), and the mixture was used as a basal medium for culture of an animal cell.

<Culture Medium A>

Thymidine and hypoxanthine were removed from a commercially available DMEM/F12 medium, and the following components were added:

30 mg/L ascorbic acid
10 mg/L deoxyadenosine ($1H_2O$)
10 mg/L deoxycytidine
10 mg/L deoxyguanosine
5 mg/L adenosine
5 mg/L cytidine
5 mg/L guanosine
5 mg/L uridine
4 mg/L ethanolamine (HCl)
1000 mg/L Pluronic F-68
18.9 mg/L ferric chloride ($6H_2O$)

To the above Culture Medium A, the enzymatic degradation product prepared in Example 2 was added in an end concentration of Brix 1% or Brix 2%, and the mixture was sterilized by filtration.

Example 4

Effect on Amount of Antibody Produced

A test was conducted using a CHO cell strain producing humanized PM-1 antibody (anti-human IL-6 receptor antibody) which was prepared in accordance with the method described in Referential Example 2 of Japanese Unexamined Patent Publication No. 99902/1996 by use of human elongation factor I$\alpha$ promotor described in Example 10 of International Patent Application Publication No. WO92/19759.

The above CHO cells ($1.5 \times 10^5$ cells/ml) were added to Culture Medium A containing the enzymatic degradation product of fish meat, which had been prepared in Example 2 herein, in a final concentration of Brix 1% or Brix 2%. The system was cultured for 10 days under the incubator conditions 37° C., 5% $CO_2$, by means of a shaker flask type cell culture device.

Then, the viable cell density, the cell survival rate, and the amount of production of an antibody protein obtained from the culture medium were measured. The amount of production was measured using reverse phase high performance liquid chromatography.

As a control, a culture medium containing 10 g/L of a beef hydrolyzate (Primatone™: Quest, United States) instead of the enzyme degradation product of Example 2 was prepared, and CHO cells were cultured in the same manner.

The results obtained are shown in FIG. 1. Compared with the control, CHO cells cultured in the culture medium containing Brix 1% of the enzymatic degradation product of bonito showed cell growth comparable-to that of the control. CHO cells cultured in the culture medium containing Brix 2% of the enzymatic degradation product of bonito obtained a larger amount of antibody protein production than the control.

Example 5

Effect of Culture Media Using Enzymatic Degradation Products of Various Fish Meats on Amount of Antibody Production Enzymatic degradation products of fish meats from bonito, sardine, salmon, frigate mackerel, cod, and mackerel were added to a culture medium of non-mammal origin, and the amount of production of antibody protein was investigated.

Preparation of Enzymatic Degradation Product of Fish Meat

An enzymatic degradation product of the above fish meat was prepared by the method described in Example 2. That is, the fish meat was minced, and enzymatically degraded with papain, a plant-derived endopeptidase. Then, the material was further enzymatically degraded with mold-derived exopeptidase, whereafter the system was heated to inactivate the enzymes. Then, the system was centrifuged and filtrated to remove insolubles and oils. The residue was concentrated to prepare an enzymatic degradation product of the fish meat.

Preparation of Culture Medium and Testing Method dhfr (−) CHO cells transformed with a gene encoding the humanized PM-1 antibody (anti-human IL-6 receptor antibody) described in Example 4, and a dhfr selective marker gene were added to Culture Medium B containing the enzymatic degradation product of bonito, sardine, salmon, frigate mackerel, cod, or mackerel in a final concentration of 10 g/L (Brix 1%) or 15 g/L (Brix 1.5%). The system was cultured for 10 days under the incubator conditions 37° C., 5% $CO_2$, by means of a shaker flask type cell culture device. Then, the viable cell density, the cell survival rate, and the amount of production of an antibody protein were measured. The components of Culture Medium B are shown below.

<Culture Medium B>

Thymidine and hypoxanthine were removed from a commercially available DMEM/F12 medium, and the following components were added:

12.5 mg/L ascorbic acid 2.5 mg/L deoxyadenosine ($1H_2O$)

2.5 mg/L deoxycytidine 2.5 mg/L deoxyguanosine 2.5 mg/L adenosine 2.5 mg/L cytidine 2.5 mg/L guanosine 5.0 mg/L uridine 0.2 mg/L putrescine (2HCl)

0.975 mg/L ethanolamine (HCl)

500 mg/L Pluronic F-68

10 mg/L Ferric Citrate

Results

Figure 4:
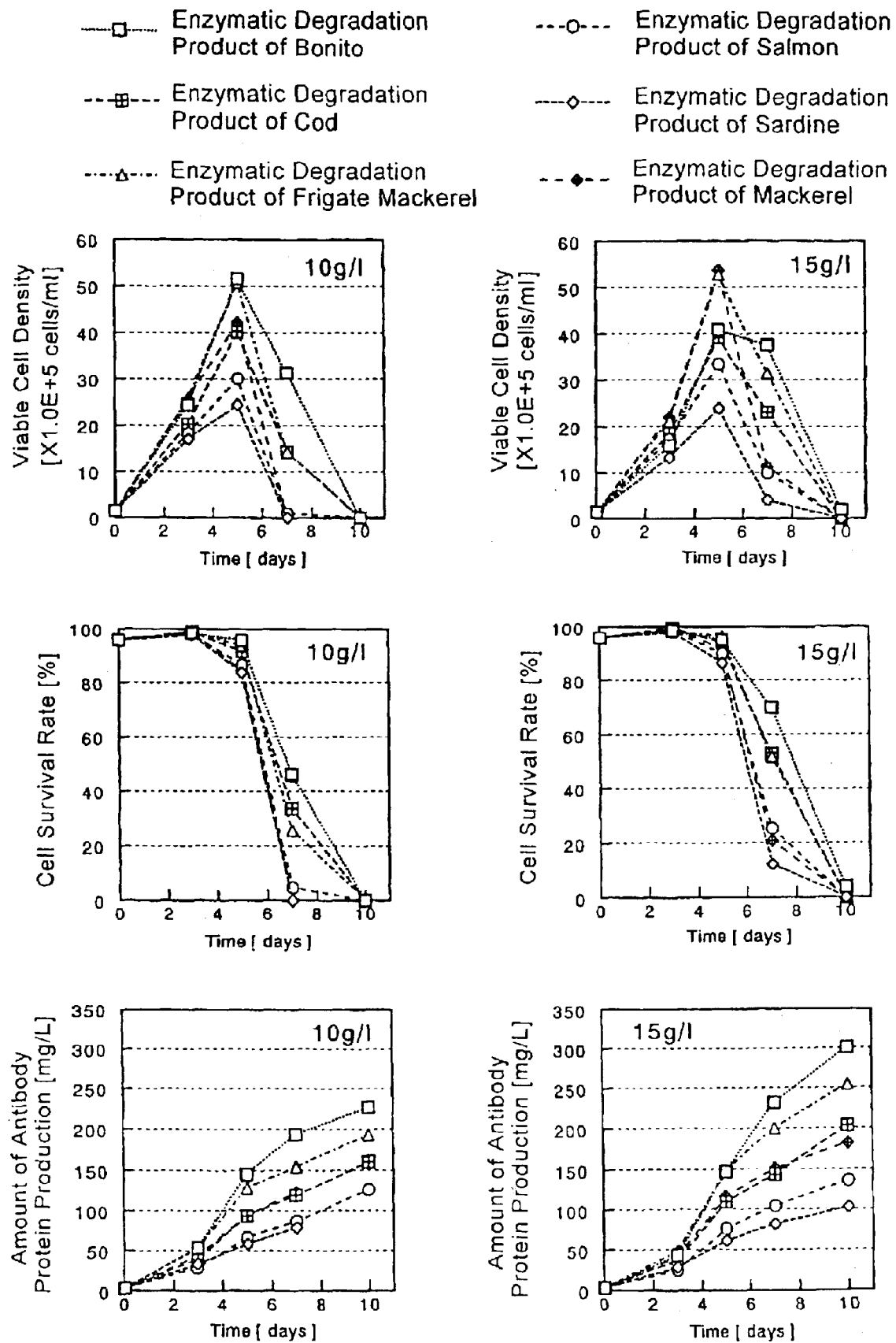
FIG. 4 shows the results of cell culture using a shaker flask type cell culture device in Example 5. The vertical axes in the panels of FIG. 4 represent the viable cell density, the cell survival rate, and the amount of an antibody protein produced, respectively. The horizontal axes each represent the number of days of culture after the start of culture using the culture medium B.

The results obtained are shown in FIG. 4. There were differences in the amount of an antibody protein produced by the fish meat hydrolyzate. That is, when the enzyme degradation product of fish meat was added in a final concentration of Brix 1% (10 g/L), the amounts produced, in decreasing order, were as follows: bonito>frigate mackerel>cod>salmon>mackerel>sardine. When the enzyme degradation product of fish meat was added in a final concentration of Brix 1.5% (15 g/L), the amounts produced, in decreasing order, were as follows: bonito>frigate mackerel>cod>mackerel>salmon>sardine.

The foregoing tests demonstrate that the enzymatic degradation product of fish meat shows different effects on the amount of antibody protein production according to the type of fish meat used, but is effective for growth of dhfr (−) CHO cells transformed with a gene encoding antibody protein and a dhfr selective marker gene, and is also effective for production of the antibody protein.

What is claimed is:

1. A serum-free culture medium for culturing an animal cell, comprising an additive, wherein said additive comprises an enzymatic hydrolysate of fish meat or a fish meat extract.

2. The culture medium of claim 1, wherein the culture medium is free from components obtained from a mammal.

3. The culture medium of claim 1, wherein said animal cell is a CHO cell.

4. The culture medium of claim 1, wherein said animal cell produces a recombinant protein.

5. A culture medium for culturing a CHO cell, wherein said culture medium comprises an enzymatic hydrolysate of fish meat or a fish meat extract.

6. The culture medium of claim 5, wherein the culture medium is free from components obtained from a mammal.

7. The culture medium of claim 5, wherein said CHO cell produces a recombinant protein.

8. A culture medium for culturing an animal cell, wherein a gene encoding a desired protein is introduced into said animal cell and said culture medium comprises an enzymatic hydrolysate of fish meat or a fish meat extract.

* * * * *